United States Patent [19]

Hobson et al.

[11] Patent Number: 5,427,921

[45] Date of Patent: Jun. 27, 1995

[54] METHOD OF PREPARING YEAST EXTRACT CONTAINING HYDROLYZED NON-YEAST PROTEIN WITH YEAST AUTOLYTIC ENZYMES

[75] Inventors: John C. Hobson; Deborah Anne G. Anderson, both of Staffordshire, United Kingdom

[73] Assignee: CPC International Inc., Englewood Cliffs, N.J.

[21] Appl. No.: 941,105

[22] PCT Filed: Apr. 19, 1991

[86] PCT No.: PCT/GB91/00617

§ 371 Date: Oct. 20, 1992

§ 102(e) Date: Oct. 20, 1992

[87] PCT Pub. No.: WO91/16447

PCT Pub. Date: Oct. 31, 1991

[30] Foreign Application Priority Data

Apr. 21, 1990 [GB] United Kingdom ............... 9009000

[51] Int. Cl.⁶ .................. C12P 21/00; C07G 17/00; A23L 1/221; A23J 1/00

[52] U.S. Cl. .................... 435/68.1; 426/49; 426/56; 426/650; 426/656; 426/657; 435/267

[58] Field of Search ............ 435/68.1, 255, 259, 435/804.41, 267; 426/60, 533, 656, 657, 650, 49, 56; 530/343

[56] References Cited

U.S. PATENT DOCUMENTS

| | | |
|---|---|---|
| 2,149,306 | 3/1939 | Millar ............................. 426/655 |
| 2,928,740 | 3/1960 | Rosenthal et al. ................. 426/60 |
| 3,645,753 | 2/1972 | Gasser ............................ 426/655 |
| 3,761,353 | 9/1973 | Noe ............................... 435/42 |
| 3,809,780 | 5/1974 | Ishida et al. .................... 435/259 |
| 3,881,022 | 4/1975 | Gasser ........................... 426/60 |
| 4,178,391 | 12/1979 | Chao ............................. 426/61 |
| 4,218,481 | 8/1980 | Chao ............................. 426/60 |

FOREIGN PATENT DOCUMENTS

| | | |
|---|---|---|
| 2292432 | 11/1974 | France . |
| 2353233 | 12/1977 | France . |
| 1074963 | 3/1989 | Japan ............................. 426/60 |
| 1179664 | 7/1989 | Japan ............................. 426/60 |
| 2171585 | 9/1986 | United Kingdom ................. 426/60 |

*Primary Examiner*—David M. Naff

[57] ABSTRACT

Non-yeast protein is mixed with yeast, and enzymatic hydrolysis is carried out with yeast autolytic enzymes and optionally added exogenous enzymes to produce a yeast extract containing hydrolyzed non-yeast protein. More specifically, a mixture of yeast cells and 5 to 50% of cereal and/or animal non-yeast protein source is maintained at 40° to 50° C. for 5 to 15 hours and then at 55° to 65° C. for 1 to 5 hours to allow enzymatic hydrolysis to produce a water-soluble fraction. The water-soluble fraction is separated and concentrated. The non-yeast protein source may be one or more of maize gluten, corn gluten, wheat gluten, soya bean meal, whey solids, dried red blood, oat bran and wheat bran. By appropriate selection of the non-yeast protein, a yeast extract with specific flavor can be produced for use as a taste additive in the food industry.

9 Claims, No Drawings

METHOD OF PREPARING YEAST EXTRACT CONTAINING HYDROLYZED NON-YEAST PROTEIN WITH YEAST AUTOLYTIC ENZYMES

The present invention relates to a process for producing yeast extracts containing a proportion of hydrolysed non-yeast protein and the product of these processes.

Yeast extract is a nutritious palatable paste prepared from brewer's or baker's yeast by autolysis. This comprises the self-digestion of the yeast cells principally through yeast proteolytic enzyme activity so that proteinaceous soluble solids can be recovered. These soluble solids are typically further concentrated to form a paste.

In order to maximise the yield of soluble solids for commercial production, yeast, such as brewer's yeast is conventionally diluted with water to a specified solids content before autolysis. Salt may also be added to the slurry to aid cell membrane rupture and exercise a degree of control over microbial flora. The yeast proteins are solubilized and hydrolysed during the autolysis process. Although the natural yeast enzymes may be sufficient to carry out the hydrolysis, the activity of the yeast proteolytic system can be augmented, if desired, by the addition of exogenous enzymes.

On completion of the autolytic process, the soluble fraction is harvested and concentrated by a series of evaporation steps to give a typical standard yeast extract. The autolytic process typically solubilises around 62% of the starting total yeast solids and yields a maximum of 80% of the yeast's original protein content.

The present invention is based on the surprising discovery that the yield of such an autolytic process can be improved and that, additionally, a range of novel flavors can be obtained by carrying out the hydrolysis on a mixture of yeast and non-yeast protein.

According to the present invention there is provided a method of making yeast extracts comprising subjecting an aqueous slurry containing a mixture of yeast protein and non-yeast protein to an at least partial enzymatic hydrolysis to form a water-soluble fraction and recovering the water-soluble fraction.

According to a preferred embodiment, the present invention comprises the steps of:

(i) forming a slurry comprising yeast solids and water;
(ii) adding from 5 to 50% by weight based on yeast and non-yeast solids of a non-yeast protein source to the slurry to form a mixture;
(iii) maintaining the mixture at a temperature of from 40° to 65° C. for from 6 to 20 hours;
(iv) separating the water-soluble fraction; and
(v) concentrating the water-soluble fraction.

The yeast protein is in the form of yeast cells and particularly preferred sources are brewer's yeast and baker's yeast. These may be used in any form (such as dried yeast) but a particularly preferred source is brewer's yeast in the form of a slurry obtained directly from the brewer.

Appropriate sources of non-yeast protein for use in the process of the invention may include sources of cereal proteins and sources of animal proteins. Preferred non-yeast protein sources include maize gluten, corn gluten, wheat gluten, soya bean meal, whey solids, soup stock and dried red blood. Additional protein sources such as oat bran and wheat bran may also be added. These non-yeast protein sources may be used directly in the hydrolysis mixture or may be further treated, by purification or protein extraction for example, before being used in the autolysis mixture. The non-yeast protein sources may be used individually or as mixtures of two or more such sources. Particularly preferred non-yeast protein sources for use in the present invention are soya bean meal and whey solids which have been found to impart surprisingly good flavors to the yeast extract products and also to be the most cost effective alternatives.

The process of the present invention results in a yield of soluble solids which is greater than can be accounted for by the yeast alone. This appears to be due to the ability of the natural proteolytic enzymes contained in the yeast to act on the non-yeast protein to solubilise and hydrolyse it. Not only does the use of added non-yeast protein enable the yield of normal autolysis procedures to be increased but the process may also be used to maintain production levels when other yeast sources are in short supply by using the non-yeast protein as a yeast protein extender. This is particularly useful when the source of yeast is brewer's yeast and this is in short supply.

By selecting appropriate non-yeast proteins, the flavor of the yeast extract may be modified to impart novel flavors to the yeast extract. Such flavors are useful in altering the taste of the yeast extract itself but may also have wide application in the food industry as taste additives, especially where ingredients of a particular character are required. The surprising novel and interesting flavors of the yeast extracts produced in the present invention are believed to be due to some form of synergistic effect resulting from the enzymatic co-hydrolysis of a mixture of yeast protein and non-yeast protein. It is believed that this is due, at least in part, to the action of yeast enzymes on both the non-yeast protein source and the yeast protein source. This is supported by the discovery that a mixture of standard yeast extract with an extract of hydrolysed soya bean meal was found to produce flavor characteristics quite different from those of the yeast extracts of the present invention.

The present invention is based on the use of yeast proteases in their natural environment and at their natural relative concentrations to break down non-yeast protein. Yeast proteases become elevated when the yeast cell is starved and begins to digest its own protein. During the process, natural inhibitors to the major yeast proteases are digested in a sequential manner thus gradually releasing more and more proteolytic activity. A cell-free system equivalent to this sequence would be extremely difficult to prepare. Yeast autolysis is thus regarded as a natural process and the present invention is based on the unexpected finding that a proportion of non-yeast protein can simultaneously be hydrolysed without reducing the yield and surprisingly imparting novel and interesting flavors to the yeast extract product.

Non-yeast proteins can be conventionally digested to varying extents using one or more commercially available protease preparations. These commercially available protease preparations are isolated, purified and concentrated from microbial sources and usually have one principle activity (e.g. NEUTRASE TM which is a serine protease). The nature of the product of such hydrolysis processes, however, is likely to be very different from the product of yeast enzyme action, both in terms of molecular weight distribution and flavor. One unique aspect of the present invention using the yeast system lies in the wide range of enzymes which are available for the hydrolysis of non-yeast protein i.e., proteases, amino peptidases and carboxypeptidases and which are naturally designed to optimize yeast protein solubilization. There is no commercial equivalent to this enzyme system. Such a sophisticated system might have been expected to be active against yeast substrates but not against non-yeast proteins. The finding that the yields were maintained (even increased) and that the resulting yeast extracts possess novel and interesting flavors was thus unexpected.

The hydrolysis or autolysis processes of the invention include, amongst other chemical changes, the cleavage of protein chains to form smaller peptides or amino acids. The hydrolysed mixture thus contains a mixture of amino acid-based material from free amino acids through peptide oligomers to longer chain proteins. The mixtures may also contain other material derived from the original starting mixture and this may include a variety of hydrolysed or unchanged material.

The process of the present invention costs approximately the same as a conventional yeast extract process since the extra yield compensates for the additional cost of the non-yeast protein.

The enzymatic hydrolysis process of the present invention may be carried out autolytically by maintaining the process conditions such that the yeast proteolytic enzymes effect the hydrolysis. Alternatively, exogenous enzymes may be added to the mixture to augment the activity of the yeast proteolytic enzymes. Suitable exogenous enzymes include plant proteases and bacterial proteases. Preferred proteases include papain and the bacterial protease made by submerged fermentation of a selected strain of *Bacillus Subtilis* and sold by Novo Nordisk Bioindustries UK Limited under the trade mark NEUTRASE ™. The exogenous enzymes may be added individually or as a mixture of different enzymes. The enzyme or enzymes may be added in varying amounts but are preferably added in an amount of from 0.003 to 0.02% by weight of the total hydrolysis mixture at around 12% yeast solids.

Typically, the non-yeast protein is used in the present invention in an amount such that the mixture of yeast and non-yeast protein, before hydrolysis, contains from 5 to 50% by weight non-yeast solids based on the total weight of yeast and non-yeast solids. If the non-yeast solids content is below 5% of the total yeast and non-yeast solids, it has been found that there is insufficient modification of the flavor of the final yeast extract product. On the other hand, if the amount of non-yeast solids exceeds 50% of the total yeast and non-yeast solids, the yeast enzymes tend to be too dilute to effect sufficient hydrolysis thus resulting in low yields of soluble solids. Preferably the mixtures contain from 10 to 45% by weight non-yeast solids based on the total weight of yeast and non-yeast solids, more preferably 15 to 40% and most preferably 30 to 35% (i.e. a ratio of yeast solids to non-yeast solids of about 2:1).

The hydrolysis process may, optionally, be carried out in the presence of sodium chloride typically in an amount of up to 1% by weight of total hydrolysis mixture. This aids in the plasmolysis of the yeast cells and inhibits the growth of microbial flora.

Although the process of the present invention may be carried out under various conditions well-known to those skilled in the art, a typical process sequence is set forth below.

An aqueous slurry containing yeast is produced by the addition of water to pressed yeast or by dilution of a 14 to 18% yeast solids slurry typically obtained from the brewery to give a 10 to 14% total solids slurry, preferably about 12% total solids. Pressed brewer's or baker's yeast typically contains from about 22% to about 35% solids and may be mixed with water in mixing vessels to produce the desired slurry composition. To this mixture is added salt in an amount not greater than 1.0% by weight of the total mixture and, optionally, one or more exogenous enzymes. This mixture is maintained under conditions which optimize the activity of at least some of the enzymes present. These conditions generally involve incubation of the mixture at a temperature of from 40° to 65° C. for from 6 to 20 hours. Preferred conditions for carrying out the hydrolysis step involve maintaining the mixture under the following conditions, sequentially:

Stage 1 : 40°-50° C. for 5 to 15 hours, particularly around 47° C. for about 10 hours;

Stage 2 : 55°-65° C. for 1 to 5 hours, particularly around 60° C. for about 2 hours;

Stage 3: at a temperature and for a length of time to pasteurise the mixture and denature the enzyme, particularly around 90° C. for about 1 hour.

It is believed that Stage 1 provides the optimum conditions for one group of yeast proteases and that Stage 2 provides the optimum conditions for a second group of yeast proteases. It is clear that these conditions may vary depending on whether exogenous enzymes are added to the mixture but the consequent alteration to the conditions would be well-known to those skilled in the art.

After hydrolysis of the mixture has been carried out, the fraction containing soluble solids is separated from the crude hydrolysis mixture. The separation can be achieved by conventional methods for separating soluble solids from crude yeast hydrolysate mixtures in the production of standard yeast extracts by autolysis. Hence, in the present invention the soluble fraction may be obtained by centrifugal separation and filtration. The resulting soluble fraction from the hydrolysis process can be concentrated by evaporation to about 40 to 50% total solids and the concentrate used as a base for process flavoring agents usually produced by controlled Maillard reactions. The soluble fraction from the hydrolysis process may, alternatively, be concentrated by evaporation to form pastes containing from 55 to 80% total solids, preferably from 70 to 80% (e.g. around 75%). Salt may optionally be added before the evaporation steps as is conventional in standard yeast extract processes.

The present invention thus provides yeast extract products having both novel and interesting flavors and a method for their production without reducing the yield of the standard autolysis process. As a result of the novel flavors possessed by these yeast extract products, there are many potential applications for the products where standard yeast extract would not achieve the same effect.

EXAMPLE 1

1200 g of brewer's yeast slurry containing 12% solids, 1% salt and 0.0094% papain by weight of total mixture was prepared and 72 g soya bean meal added. The whole was then autolysed with stirring at 47° C. for 10 hours followed by 60° C. for 2 hours followed by 90° C. for 1 hour.

The soluble solids fraction was separated and evaporated and the final extract prepared in the manner conventionally used for yeast extract.

The results were as follows:

|  | Raw Material Cost | Recovered Solubles | Raw Material Cost/100 g Recovered Solubles |
|---|---|---|---|
| Control (1200 g yeast slurry) | 0.028 | 65.7 g | 0.0426 |
| + Soya bean meal (1200 g yeast slurry +72 g Soya bean meal) | 0.045 | 91.1 g (+39%) | 0.0494 |

EXAMPLE 2

Details as for Example 1 except that whey solids are used instead of soya bean meal.

The results were as follows:

|  | Raw Material Cost | Recovered Solubles | Raw Material Cost/100 g Recovered Solubles |
|---|---|---|---|
| Control (1200 g yeast slurry) | 0.028 | 65.7 g | 0.0426 |
| + Whey Solids (1200 yeast slurry + 72 g whey solids) | 0.046 | 98.2 g (+49%) | 0.0468 |

Thus, Examples 1 and 2 both demonstrate that increased raw material cost is compensated for by a significant increase in recovered soluble.

In both cases, final extracts of the cohydrolysates were described by expert assessors as having interesting novel flavors not usually associated with brewers yeast extract.

EXAMPLE 3

1500 g of brewers yeast slurry containing 12% yeast solids and 1% salt by weight of total mixture was prepared and 60 g maize gluten granules were added. Papain was added and the mixture autolysed with stirring at 47° C. for 10 hours followed by 60° C. for 2 hours followed by 90° C. for 1 hour. 10 The soluble solids fraction was separated and evaporated and the final extract prepared in the manner conventionally used for yeast extract, adjusting the salt level to about 12% before the final evaporation.

We claim:

1. A method of making yeast extract containing hydrolyzed non-yeast protein, comprising the steps of:
    (i) forming a slurry comprising 10 to 14% yeast cell solids and water;
    (ii) adding to the slurry a non-yeast protein source selected from the group consisting of a cereal protein source, an animal protein source and mixture thereof in an amount of from 5 to 50% by weight based on yeast and non-yeast protein source solids to form a mixture;
    (iii) maintaining the mixture at a temperature of from 40° to 50° C. for 5 to 15 hours, and then at a temperature of from 55° to 65° C. for a period of from 1 to 5 hours to allow enzymatic hydrolysis to proceed to form a water-soluble fraction;
    (iv) separating the water-soluble fraction; and
    (v) concentrating the water-soluble fraction.
2. The method as claimed in claim 1, wherein the hydrolysis is autolytic without added exogenous enzymes.
3. The method as claimed in claim 1, wherein exogenous enzymes are added to the mixture.
4. The method as claimed in claim 1, wherein the source of non-yeast protein is selected from the group consisting of maize gluten, corn gluten, wheat gluten, soya bean meal, whey solids, dried red blood, oat bran, wheat bran and mixtures thereof.
5. The method as claimed in claim 1, wherein the mixture contains up to 1% by weight salt.
6. The method as claimed in claims 1, wherein the water-soluble fraction is pasteurized.
7. The method as claimed in claims 1, wherein the water-soluble fraction is concentrated by evaporation to from 40 to 50% total solids.
8. The method as claimed in claim 1, wherein the water-soluble fraction is concentrated by evaporation to form a paste comprising from 55 to 80% total solids.
9. The yeast extract containing hydrolyzed non-yeast protein produced by the method of claim 1.

* * * * *